US012697114B2

(12) United States Patent
Khalil et al.

(10) Patent No.: US 12,697,114 B2
(45) Date of Patent: Aug. 4, 2026

(54) SCAFFOLD AND SUTURE ANCHORING DEVICE

(71) Applicant: AEVUMED, INC., Malvern, PA (US)

(72) Inventors: Saif Khalil, Malvern, PA (US); Miles Curtis, Berwyn, PA (US); Eric Black, Livingston, NJ (US); Grant Edward Garrigues, Hinsdale, IL (US); Robert James Gillespie, Shaker Heights, OH (US); Anand Murugan Murthi, Lutherville, MD (US); Surena Namdari, Gladwyne, PA (US); Eric Jason Strauss, Scarsdale, NY (US)

(73) Assignee: AEVUMED, INC., Malvern, PA (US)

( * ) Notice: Subject to any disclaimer, the term of this patent is extended or adjusted under 35 U.S.C. 154(b) by 444 days.

(21) Appl. No.: 17/692,715

(22) Filed: Mar. 11, 2022

(65) Prior Publication Data

US 2022/0287707 A1    Sep. 15, 2022

Related U.S. Application Data

(60) Provisional application No. 63/160,708, filed on Mar. 12, 2021.

(51) Int. Cl.
*A61B 17/04* (2006.01)
*A61B 17/00* (2006.01)
*A61B 17/29* (2006.01)

(52) U.S. Cl.
CPC ...... *A61B 17/0469* (2013.01); *A61B 17/2909* (2013.01); *A61B 2017/00893* (2013.01); *A61B 2017/0409* (2013.01)

(58) Field of Classification Search
CPC ...... A61B 2017/048; A61B 2017/0495; A61B 2017/0406; A61B 17/0469; A61B 17/2909; A61B 2017/00893; A61B 2017/0464
See application file for complete search history.

(56) References Cited

U.S. PATENT DOCUMENTS

| | | | |
|---|---|---|---|
| 6,533,795 B1 | 3/2003 | Tran |
| 6,551,330 B1 | 4/2003 | Bain |
| 7,166,116 B2 | 1/2007 | Lizardi |
| 7,758,597 B1 | 7/2010 | Tran |
| 7,842,050 B2 | 11/2010 | Diduch |
| 7,879,046 B2 | 2/2011 | Weinert |
| 7,938,839 B2 | 5/2011 | Difrancesco |
| 8,177,796 B2 | 5/2012 | Akyuz |
| 8,460,318 B2 | 6/2013 | Murray |
| 8,663,250 B2 | 3/2014 | Weber |
| 8,690,898 B2 | 4/2014 | Hatch |
| 9,011,454 B2 | 4/2015 | Hendricksen |
| 9,610,075 B2 | 4/2017 | Heneveld |
| 9,668,726 B1 | 6/2017 | Bourland, III |
| 9,687,225 B2 | 6/2017 | Palese |

(Continued)

*Primary Examiner* — Brooke Labranche
*Assistant Examiner* — Rachael L Geiger
(74) *Attorney, Agent, or Firm* — Riverside Law LLP

(57) ABSTRACT

The present invention provides scaffold and suture anchoring devices for anchoring scaffolds and sutures into a target site such as soft tissue. The devices include a retainer mechanism that holds the scaffolds in a grasper and can be actuated to release the scaffolds from the grasper. The devices include retractable needles that can be actuated to pass suture threads through the grasper to anchor scaffolds to a target site.

19 Claims, 12 Drawing Sheets

(56)  References Cited

U.S. PATENT DOCUMENTS

| | | | |
|---|---|---|---|
| 10,052,098 B2 | 8/2018 | Hatch | |
| 2002/0045908 A1* | 4/2002 | Nobles ............... | A61B 17/0057 |
| | | | 606/144 |
| 2006/0004388 A1* | 1/2006 | Whayne ............... | A61B 17/122 |
| | | | 606/151 |
| 2007/0179528 A1* | 8/2007 | Soltz ................ | A61B 17/07292 |
| | | | 227/175.1 |
| 2008/0296345 A1* | 12/2008 | Shelton, IV ..... | A61B 17/07207 |
| | | | 227/176.1 |
| 2011/0040308 A1* | 2/2011 | Cabrera ............ | A61B 17/0491 |
| | | | 606/144 |
| 2012/0288530 A1* | 11/2012 | Bordoloi ................... | A61P 9/14 |
| | | | 514/21.2 |

* cited by examiner

1

SCAFFOLD AND SUTURE ANCHORING DEVICE

CROSS-REFERENCE TO THE RELATED APPLICATIONS

This application claims priority to U.S. Provisional Patent Application No. 63/160,708 filed Mar. 12, 2021, the contents of which are incorporated by reference herein in its entirety.

BACKGROUND OF THE INVENTION

Soft tissue tears are common and many repair methods rely solely on the mechanical attributes of fasteners to repair the soft tissue. However, the fasteners alone are inadequate for proper healing, as the soft tissue is in a weakened state and penetrating the soft tissue with the fasteners merely introduces additional weak points that are prone to further tearing.

Thus, there is a need in the art for improved devices that anchor scaffolds with suture to target tissue to enhance repair and healing. The present invention meets this need.

SUMMARY OF THE INVENTION

In one aspect, the present invention relates to a scaffold and suture anchoring device, comprising: an elongated shaft having a proximal end and a distal end; a handle connected to the proximal end of the shaft, the handle comprising a grasper trigger, a needle trigger, and a retainer tab slot; a grasper comprising an upper jaw hingedly connected to a lower jaw at the distal end of the shaft, the grasper being mechanically linked to the grasper trigger; a retainer positioned within a lumen of the shaft, the retainer comprising at least one retainer tab slidable in the retainer tab slot at a proximal end and at least one retainer tine extending through the upper jaw and the lower jaw of the grasper at a distal end; and at least one needle positioned within a needle channel of the shaft, the needle being mechanically linked to the needle trigger; wherein the needle channel extends to the lower jaw of the grasper and curves towards at least one needle channel opening facing the upper jaw of the grasper.

In one embodiment, the device further comprises at least one suture thread pre-threaded onto the at least one needle. In one embodiment, the upper jaw comprises a window facing the lower jaw of the grasper, such that the at least one needle channel opening is enclosed by the window when the grasper is in a closed position.

In one embodiment, the grasper trigger comprises a lock configured to lock an instant position of the grasper. In one embodiment, the mechanical link between the grasper trigger and the grasper comprises a spring force configured to return the grasper to an open position. In one embodiment, the needle trigger comprises a lock configured to lock an instant position of the needle. In one embodiment, the mechanical link between the needle trigger and the needle comprises a spring force configured to return the needle to a retracted position.

In one embodiment, the device further comprises at least one scaffold preloaded onto the grasper. In one embodiment, the at least one scaffold is secured between the upper jaw of the grasper and the at least one retainer tine. In one embodiment, the at least one scaffold is secured between the lower jaw of the grasper and the at least one retainer tine. In one embodiment, the at least one scaffold is constructed from a synthetic material selected from the group consisting of: poly(urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), poly(methacrylic acid), polylactic acid (PLA), polyglycolic acids (PGA), poly(lactide-co-glycolides) (PLGA), nylons, polyamides, polyanhydrides, poly(ethylene-co-vinyl alcohol) (EVOH), polycaprolactone, poly(vinyl acetate) (PVA), polyvinylhydroxide, poly(ethylene oxide) (PEO), polyorthoesters, and combinations thereof. In one embodiment, at least one scaffold comprises an anisotropic material. In one embodiment, the at least one scaffold comprises a biological material selected from the group consisting of: collagen, fibrin, fibrinogen, thrombin, elastin, laminin, fibronectin, hyaluronic acid, chondroitin 4-sulfate, chondroitin 6-sulfate, dermatan sulfate, heparin sulfate, heparin, and keratan sulfate, proteoglycans, polysaccharides (e.g., cellulose and its derivatives), chitin, chitosan, alginic acids, alginates, and combinations thereof. In one embodiment, the at least one scaffold further comprises a factor selected from the group consisting of: epidermal growth factor (EGF), platelet derived growth factor (PDGF), basic fibroblast growth factor (bFGF), transforming growth factor-β (TGF-β), tissue inhibitors of metalloproteinases (TIMP), antibiotics, bacteriocides, fungicides, silver-containing agents, analgesics, nitric oxide releasing compounds, and combinations thereof. In one embodiment, the at least one scaffold further comprises a population of cells selected from the group consisting of: fibroblasts, osteoblasts, keratinocytes, epithelial cells, endothelial cells, mesenchymal stem cells, embryonic stem cells, and combinations thereof.

In one aspect, the present invention relates to a method of anchoring at least one scaffold and suture thread to a target tissue, comprising the steps of: closing a grasper end of a tool on a target tissue such that at least one scaffold held within the grasper end is pressed against the target tissue; actuating at least one needle through the grasper end of the tool, wherein the at least one needle passes at least one suture thread through the at least one scaffold and the target tissue; and releasing the at least one scaffold from the grasper end of the tool such that the at least one scaffold and the at least one suture thread remain on the target tissue.

In one embodiment, the step of closing the grasper end of the tool can be repeated prior to the step of actuating at least one needle. In one embodiment, the step of closing the grasper end of the tool further comprises a step of locking the grasper end of the tool such that the grasper end remains closed on the target tissue until the lock is released. In one embodiment, the method further comprises a step of retrieving the at least one suture thread after the step of actuating the at least one needle. In one embodiment, the step of releasing the at least one scaffold from the grasper end of the tool is performed by sliding retainer tabs of a retainer to withdraw retainer tines from the grasper end of the tool.

BRIEF DESCRIPTION OF THE DRAWINGS

The following detailed description of exemplary embodiments of the invention will be better understood when read in conjunction with the appended drawings. It should be understood, however, that the invention is not limited to the precise arrangements and instrumentalities of the embodiments shown in the drawings.

DETAILED DESCRIPTION

Figure 1:
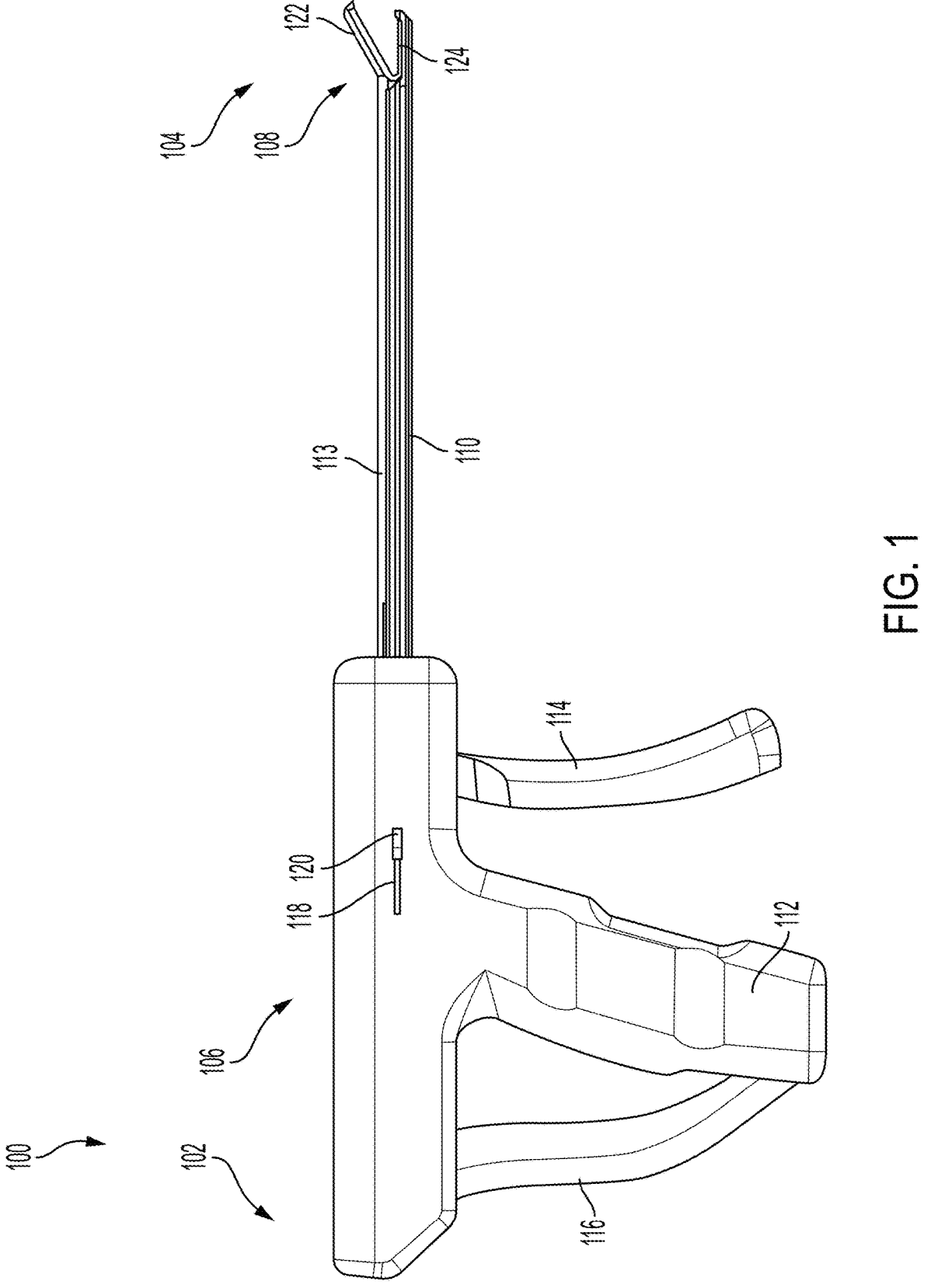
FIG. 1 depicts a side view of an exemplary scaffold and suture anchoring device.

The present invention provides scaffold and suture anchoring devices with for anchoring scaffolds and sutures into a target site such as soft tissue. The devices include a retainer mechanism that holds the scaffolds in a grasper and can be actuated to release the scaffolds from the grasper. The devices include retractable needles that can be actuated to pass suture threads through the grasper to anchor scaffolds to a target site.

Definitions

It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein.

The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments there between. This applies regardless of the breadth of the range.

Scaffold and Suture Anchoring Device

Referring now to FIG. 1, an exemplary scaffold and suture anchoring device 100 is depicted. Device 100 comprises a handle 106 at a proximal end 102 and a grasper 108 at a distal end 104. Handle 106 comprises a housing 112 holding the internal components and mechanisms of device 100, as well as a grasper trigger 114 and a needle trigger 116. Handle 106 further comprises a lateral slot 118 through which retainer tab 120 is slidable in proximal and distal directions. Handle 106 is connected to grasper 108 by a shaft 110. Shaft 110 can have any suitable length and diameter. For example, in arthroscopic use cases, shaft 110 can have a length between about 10 cm and 100 cm and a diameter sized to fit within an arthroscopic port, while in non-arthroscopic use cases, shaft 110 can have a length between about 1 cm and 10 cm.

Figure 2:
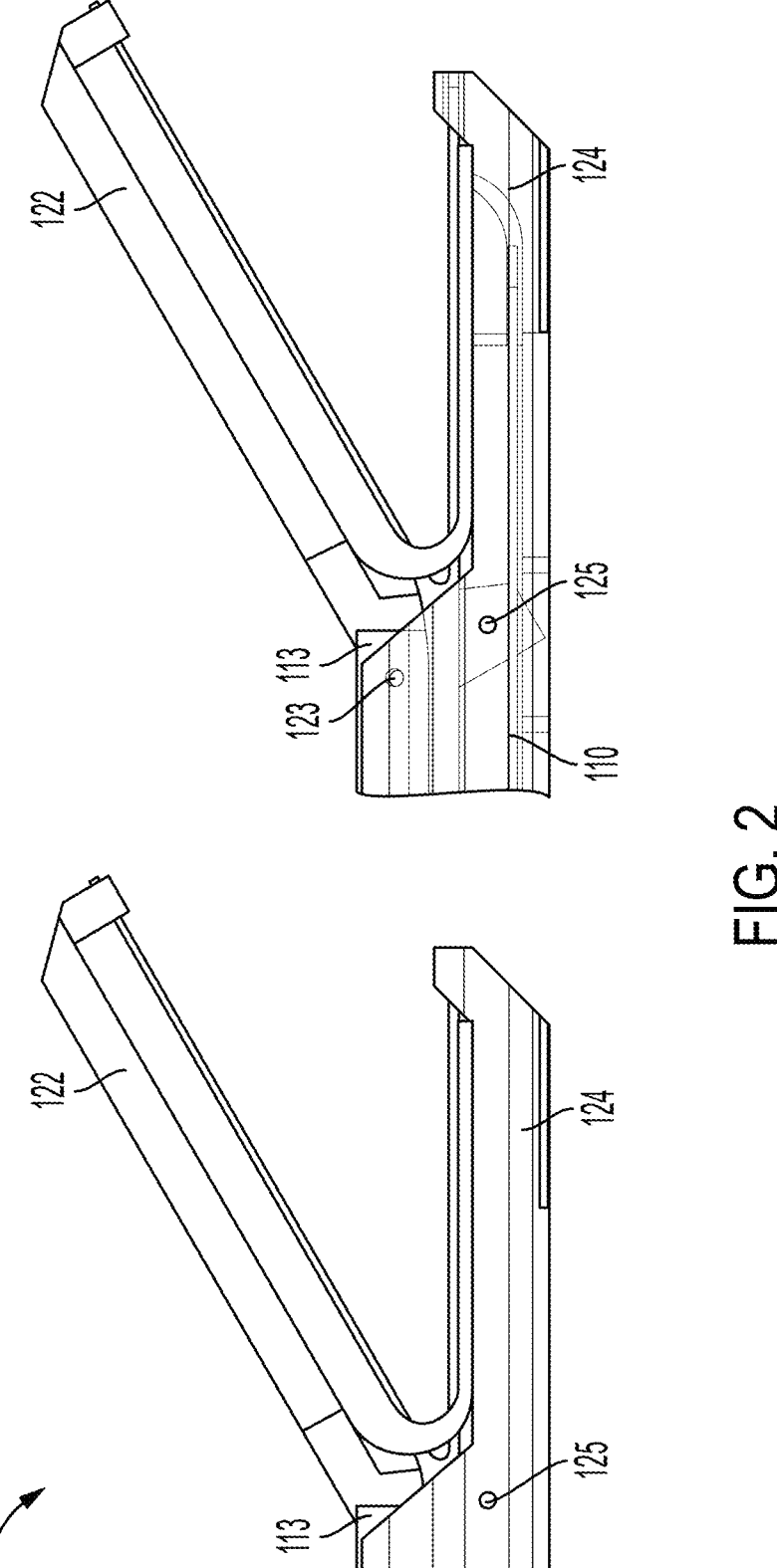
FIG. 2 depicts side views of a grasping end of an exemplary scaffold and suture anchoring device, wherein a top jaw is highlighted (left) and a shaft is shown as partially transparent to reveal the interior of the shaft (right).
Figure 3:
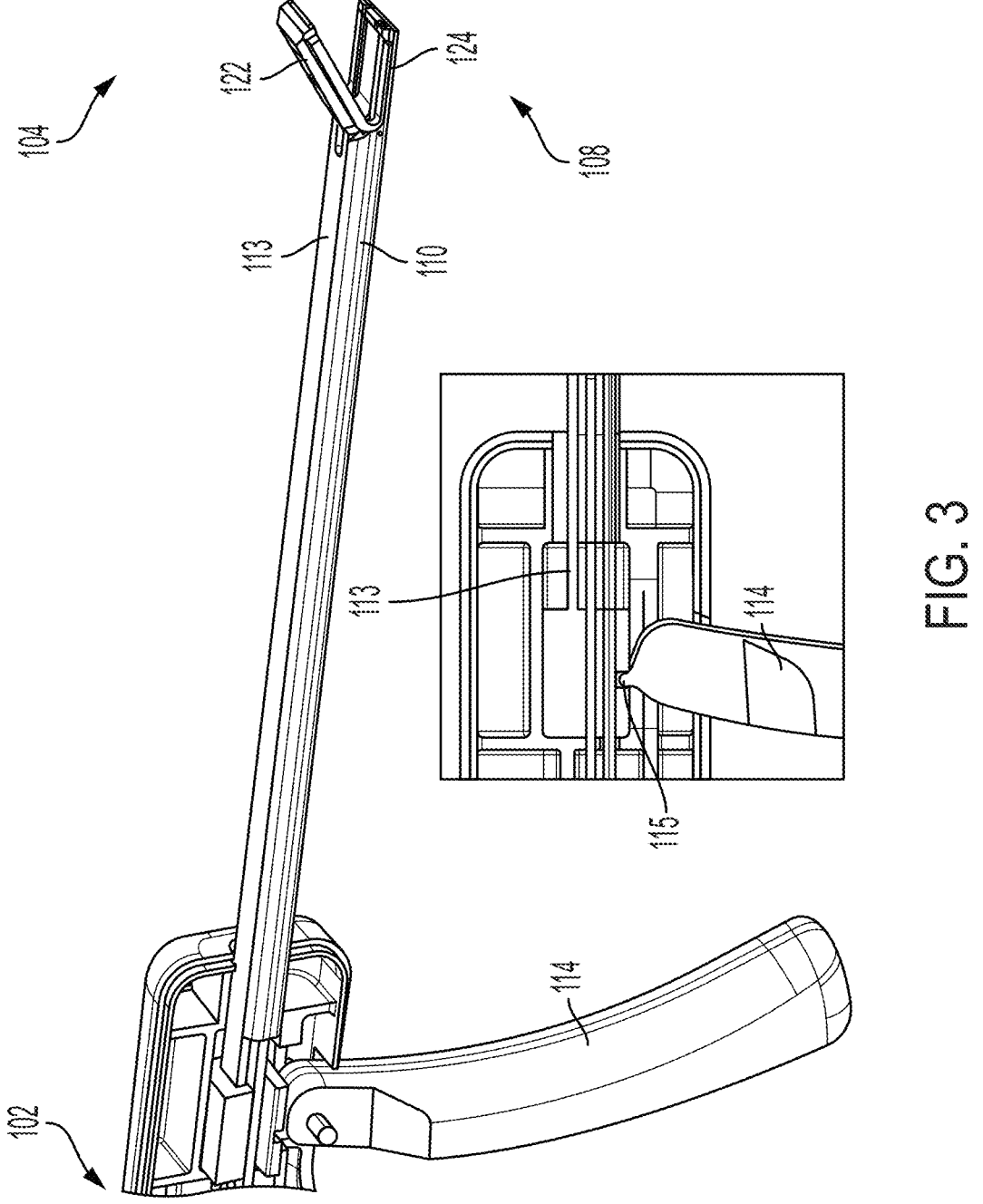
FIG. 3 depicts a perspective cutaway view of an exemplary scaffold and suture anchoring device highlighting a grasper arm and grasper trigger to illustrate the mechanism of opening and closing the grasper end (inset).

Referring now to FIG. 2, grasper 108 comprises upper jaw 122 connected to lower jaw 124 by a lower jaw hinge 125, wherein upper jaw 122 and lower jaw 124 are actuated by a mechanical or electronic link extending through a lumen of shaft 110 to grasper trigger 114. For example, upper jaw 122 can be connected go a grasper arm 113 by an upper jaw hinge 123, wherein grasper arm 113 extends to handle 106 and is engaged to grasper trigger 114 by a tab and slot 115 connection or other geared connection (FIG. 3). Grasper trigger 114 is thereby configured to push grasper arm 113 in a distal direction when pulled, which in turn pushes upper jaw 122 to rotate about lower jaw hinge 125 and close grasper end 108. In various embodiments, the mechanical or electronic link between grasper trigger 114 and grasper 108 comprises a lock, such that an instant position of upper jaw 122 relative to lower jaw 124 can be maintained in place and released using the lock. The instant position can be a fully open position, a fully closed position, and any position in between. In some embodiments, the mechanical or electronic link between grasper trigger 114 and grasper 108 comprises a spring that applies a spring force that returns grasper 108 to a fully open position upon release of the lock, grasper trigger 114, or both. Alternatively, the spring force can return grasper 108 to a full close position. In some embodiments, upper jaw 122 and lower jaw 124 are each actuatable. In some embodiments, one jaw is actuatable while the opposing jaw is stationary.

Figure 4:
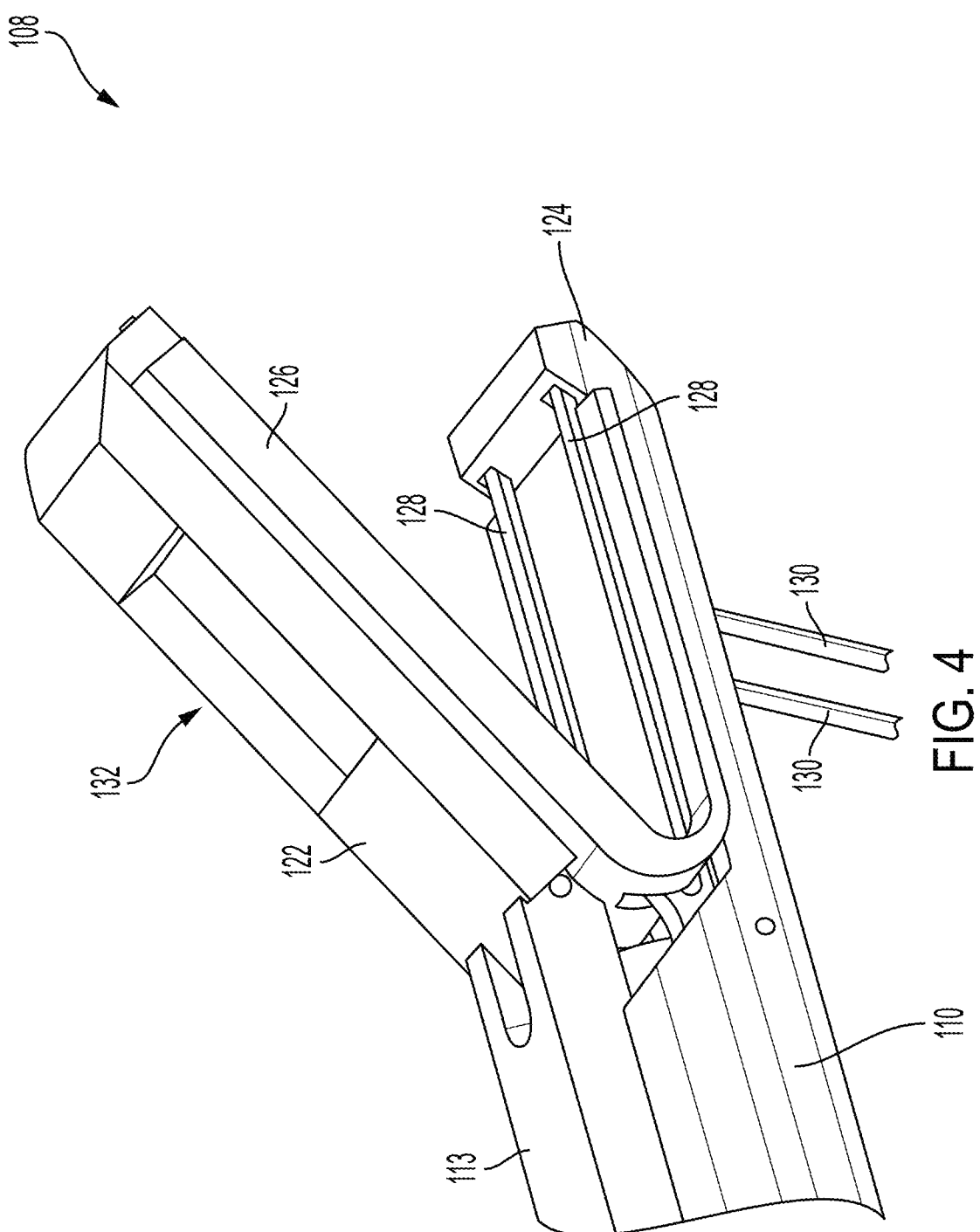
FIG. 4 depicts a magnified view of a grasping end of an exemplary scaffold and suture anchoring device, wherein an exemplary scaffold is highlighted.

Referring now to FIG. 4, a magnified view of grasper 108 is shown. Grasper 108 is configured to retain a scaffold 126 (highlighted for visibility) between upper jaw 122 and lower jaw 124 using a plurality of retainer tines 128. At least one suture thread 130 is shown descending from lower jaw 124. In some embodiments, suture thread 130 is preloaded onto lower jaw 124, as described elsewhere herein. In some embodiments, suture thread 130 can be pre-threaded on a portion of scaffold 126 retained in lower jaw 124. Opposite the location of suture thread 130, upper jaw 122 comprises a window 132 through which one or more needles 117 can pass through, as described elsewhere herein.

In various embodiments, scaffold 126 can be preloaded onto grasper 108 for delivery to a target site. Scaffold 126 can have any desired shape, including but not limited to square, rectangular, polygonal, circular, ovoid, and irregularly shaped sheets. While the depicted scaffold 126 comprises a single construct folded between upper jaw 122 and lower jaw 124, it should be understood that any number of scaffolds 126 can be held within grasper 108 by retainer tines 128. Non-limiting examples include one or more scaffolds 126 retained in upper jaw 122 and one or more scaffolds 126 retained in lower jaw 124.

Scaffold 126 can be configured to heal or repair a target site. For example, scaffold 126 can be used to wrap around a soft tissue such as a tendon or ligament for secure attachment to a bone surface. Scaffold 126 can comprise synthetic materials, biological materials, and combinations thereof to enhance biocompatibility and healing. Contemplated synthetic materials include but are not limited to: poly(urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), poly(methacrylic acid), polylactic acid (PLA), polyglycolic acids (PGA), poly(lactide-co-glycolides) (PLGA), nylons, polyamides, polyanhydrides, poly(ethylene-co-vinyl alcohol) (EVOH), polycaprolactone, poly(vinyl acetate) (PVA), polyvinylhydroxide, poly(ethylene oxide) (PEO) and polyorthoesters or any other similar synthetic polymers that may be developed that are biologically compatible. Contemplated biological materials include but are not limited to: collagen (e.g. Type I with Type II, Type I with Type III, Type II with Type III, etc.), fibrin, fibrinogen, thrombin, elastin, laminin, fibronectin, hyaluronic acid, chondroitin 4-sulfate, chondroitin 6-sulfate, dermatan sulfate, heparin sulfate, heparin, and keratan sulfate, proteoglycans, polysaccharides (e.g. cellulose and its derivatives), chitin, chitosan, alginic acids, and alginates such as calcium alginate and sodium alginate. In some embodiments, scaffold 126 comprises tissue grafts. In some embodiments, scaffold 126 comprises isotropic materials. In other embodiments, scaffold 126 comprises anisotropic fibers, such that scaffold 126 can be positioned in a direction that aligns anisotropic fibers in a direction of natural or expected anatomic forces to resist tearing and further damage.

In various embodiments, scaffold 126 can be embedded or conjugated with factors that promote healing, including but not limited to epidermal growth factor (EGF), platelet derived growth factor (PDGF), basic fibroblast growth factor (bFGF), transforming growth factor-β (TGF-β), and tissue inhibitors of metalloproteinases (TIMP). Additional factors can include antibiotics, bacteriocides, fungicides, silver-containing agents, analgesics, and nitric oxide releasing compounds. Scaffold 126 may also be seeded with cells, such as fibroblasts, osteoblasts, keratinocytes, epithelial cells, endothelial cells, mesenchymal stem cells, and/or embryonic stem cells.

Figure 5:
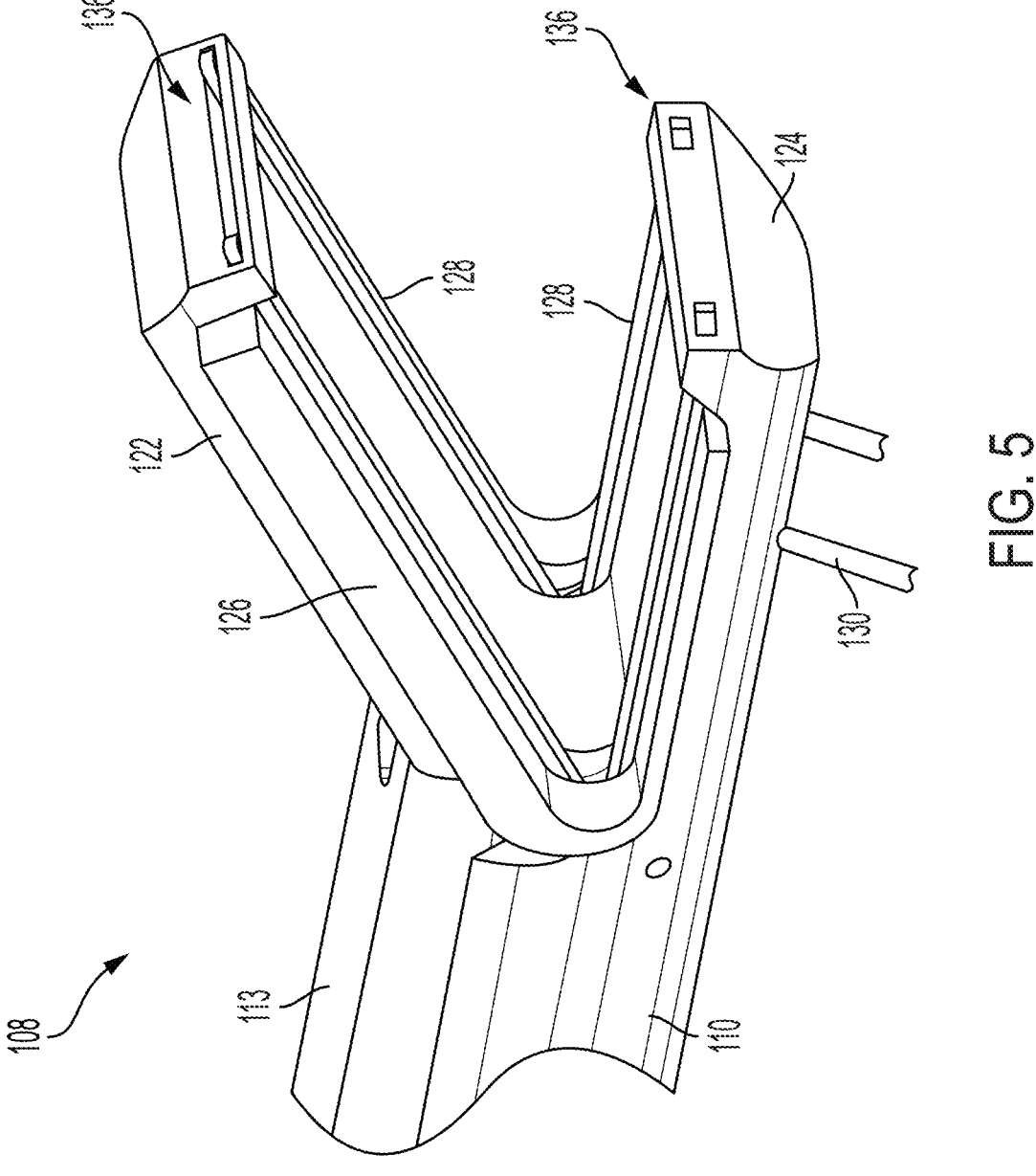
FIG. 5 depicts a magnified view of a grasping end of an exemplary scaffold and suture anchoring device, wherein tines of an exemplary scaffold retainer are highlighted.

Referring now to FIG. 5, another magnified view of grasper 108 is shown. Retainer tines 128 (highlighted for visibility) extend out of shaft 110 and over portions of scaffold 126 to retain scaffold 126 against upper jaw 122 and lower jaw 124. In some embodiments, retainer tines 128 extend through tine slots 136 positioned at distal tips of upper jaw 122, lower jaw 124, or both.

Figure 6:
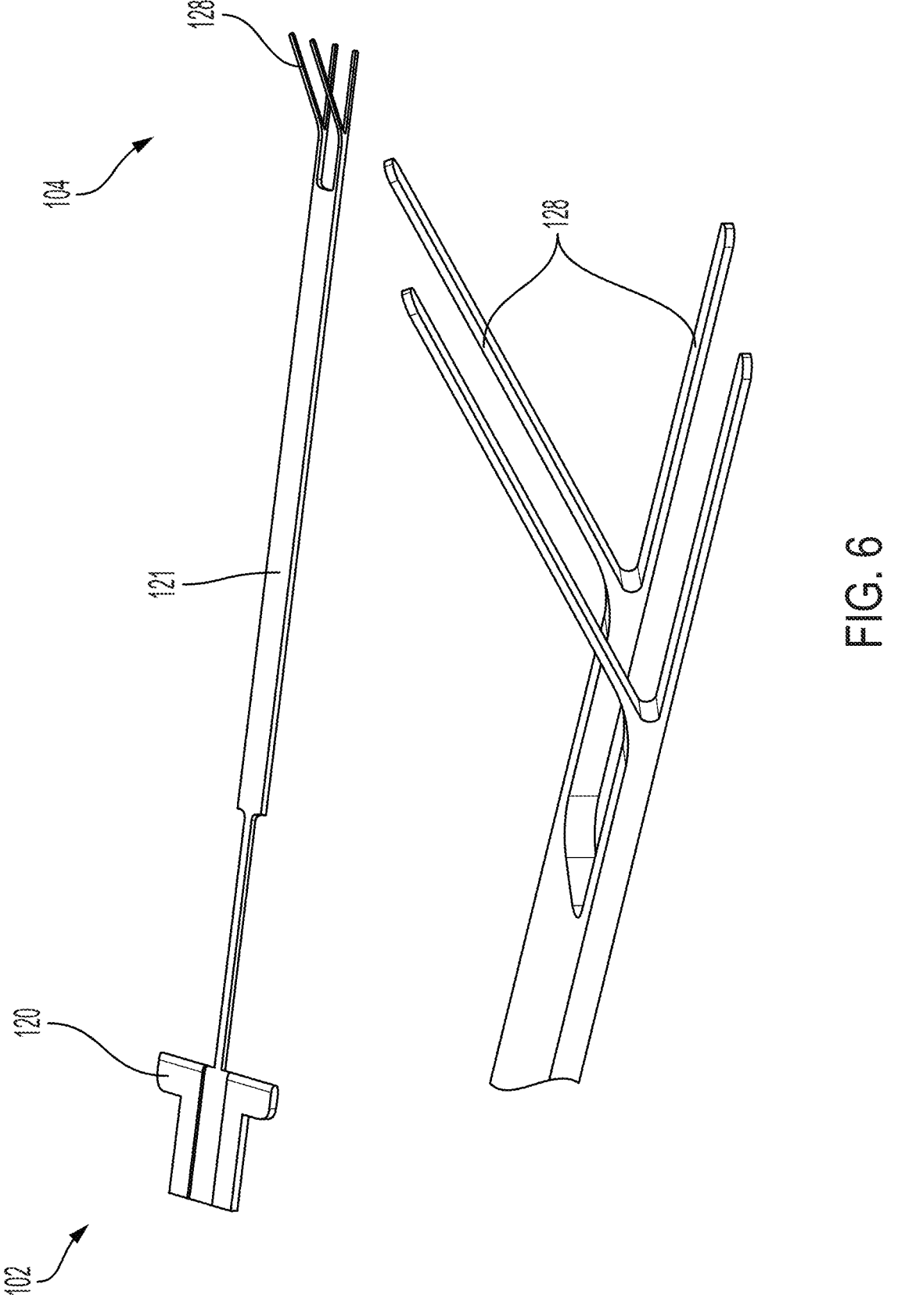
FIG. 6 depicts a perspective view (top) of an exemplary scaffold retainer in isolation and a magnified view (bottom) of the tines of an exemplary scaffold retainer.

Referring now to FIG. 6, retainer 121 is now described. Retainer 121 comprises retainer tabs 120 at proximal end 102 and retainer tines 128 at distal end 104. Retainer 121 is constructed from a flexible material such that retainer tines 128 flex with opening and closing of grasper 108, such as a hard polymer or thin metal. In some embodiments, retainer 121 is at least partially constructed from a shape memory material such as nitinol. Retainer tines 128 can be withdrawn from grasper 108 by sliding retainer tabs 120 in a proximal direction through slot 118 of handle 106. Withdrawing retainer tines 128 frees and releases scaffold 126 from grasper 108, as will be described elsewhere herein.

Figure 7:
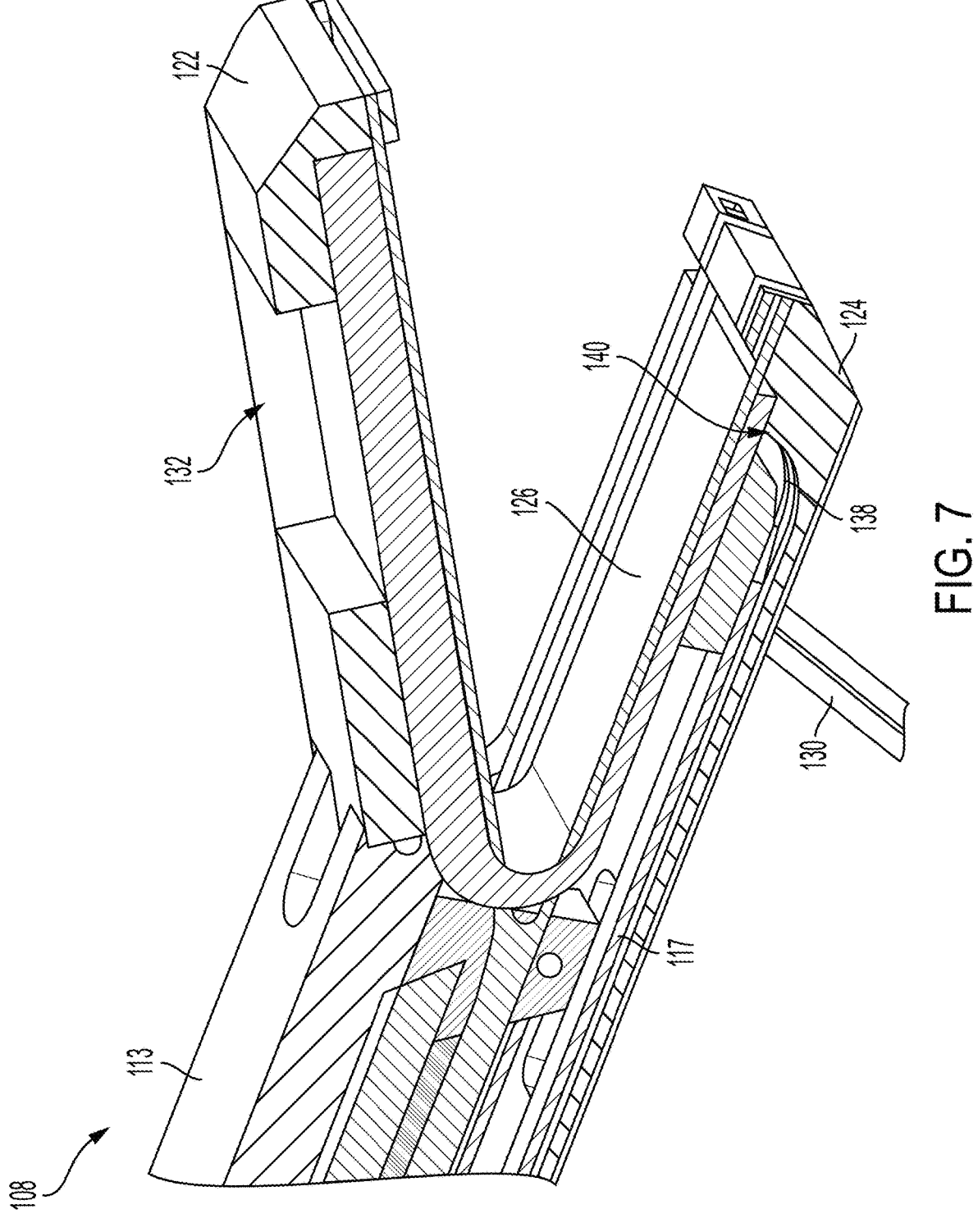
FIG. 7 depicts a perspective cutaway view of a grasping end of an exemplary scaffold and suture anchoring device, wherein an exemplary needle in a needle channel is visible.

Referring now to FIG. 7, a cutaway view of grasper 108 is shown, revealing needle 117 (highlighted for clarity). Needle 117 is constructed from a material configured to make arcuate bends while having sufficient stiffness to penetrate soft tissue, such as a hard polymer or thin metal. In some embodiments, needle 117 is at least partially constructed from a shape memory material such as nitinol, wherein needle 117 is provided with a preformed arcuate shape that is constrained as straight within needle channel 138 in a retracted position. In some embodiments, needle 117 can be provided with a preformed straight shape that conforms to curvatures of needle channel 138. Needle 117 is actuated by a mechanical or electronic link extending through a lumen of shaft 110 to needle trigger 116, wherein actuation of needle 117 pushes a distal tip through needle channel 138, out of needle channel opening 140, and towards an opposing jaw of grasper 108. In various embodiments, the mechanical or electronic link between needle trigger 116 and needle 117 comprises a lock, such that an instant position of needle 117 can be maintained in place and released using the lock. The instant position can be a fully retracted position of needle 117, a fully extended position of needle 117, and any position in between. In some embodiments, the mechanical or electronic link between needle trigger 116 and needle 117 comprises a spring that applies a spring force that returns needle 117 to a fully retracted position upon release of the lock, needle trigger 116, or both.

Figure 8:
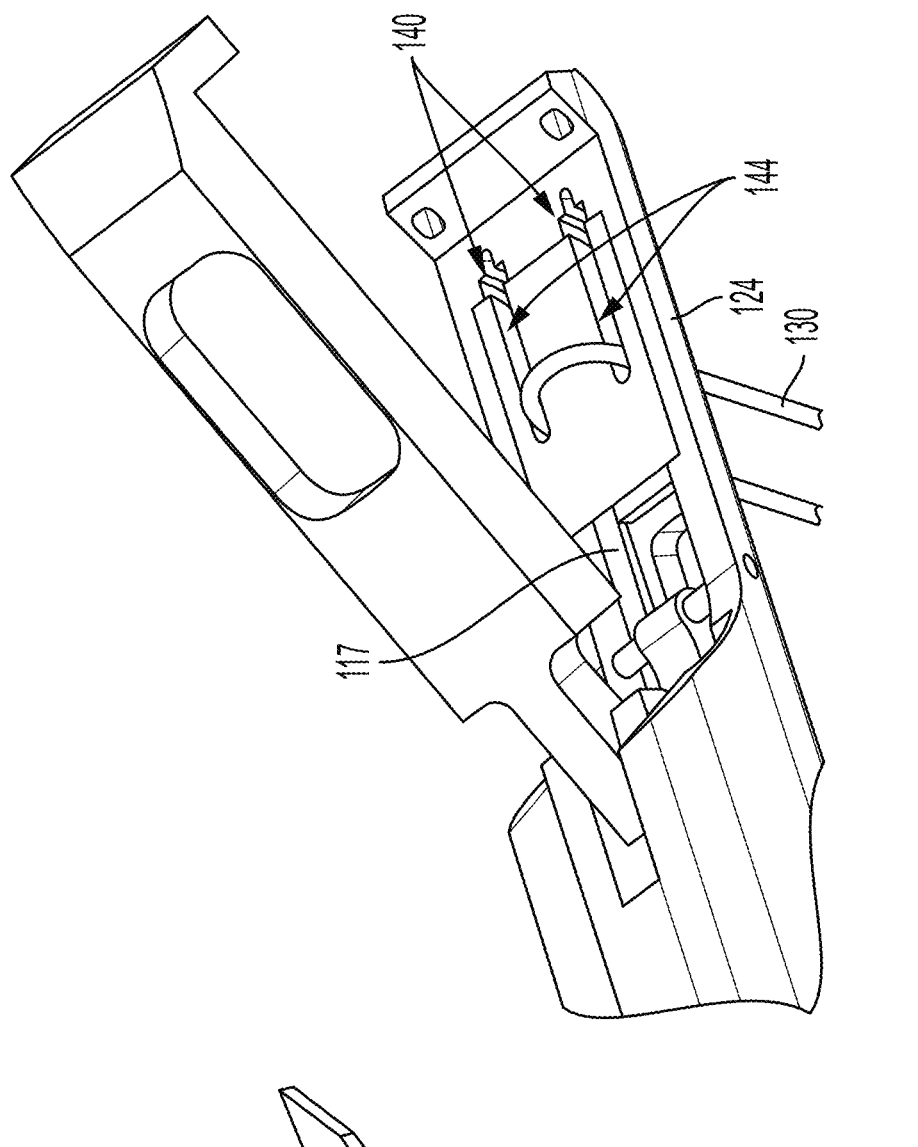
FIG. 8 depicts (left) an exemplary needle in isolation pre-threaded with a suture thread and (right) a magnified view of a suture thread pre-threaded through thread slots and needle channel openings in a grasping end of an exemplary scaffold and suture anchoring device.
Figure 8:
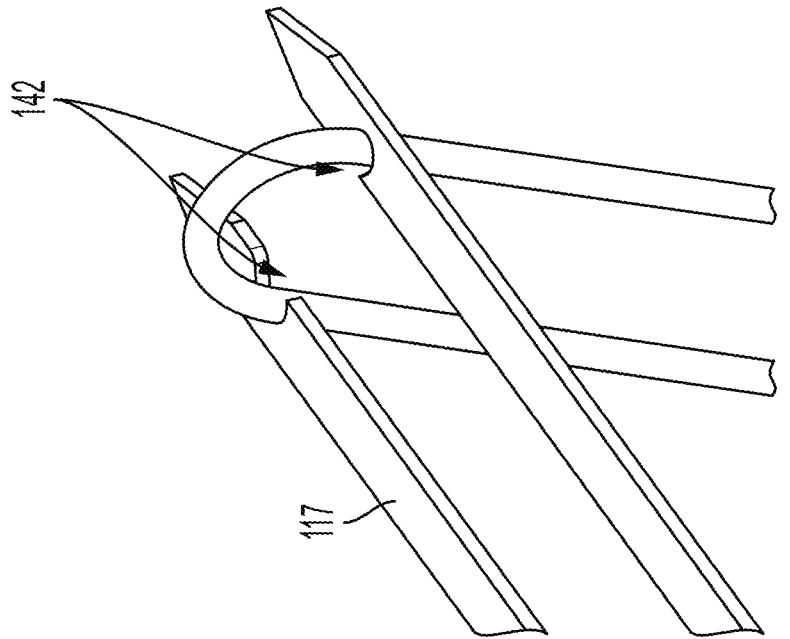

Visible in FIG. 8 (left), needle 117 comprises a catch 142 configured to hold a suture thread 130. Catch 142 can have any suitable shape, such as a hook, a notch, an eyelet, or some other transverse opening. In some embodiments, catch 142 can face inwards in a medial direction, outwards in opposing lateral directions, or combinations thereof. FIG. 8

(right) shows needle channel openings 140 for each distal tip of needle 117. While needle 117 is depicted having two tips, it should be understood that needle 117 can have any desired number of tips (with a respective jaw comprising an appropriate number of needle channels 138 and needle channel openings 140). FIG. 8 (right) also shows lower jaw 124 comprising thread slots 144 that hold a suture thread 130. In some embodiments, lower jaw 124 is provided having suture threads 130 pre-threaded through thread slots 144. In some embodiments, a portion of lower jaw 124 between thread slots 144 is removable to facilitate loading and removal of suture thread 130. In some embodiments, the removable portion can be presented in cartridge form having one or more suture threads 130 preloaded to facilitate loading of suture thread 130.

In some embodiments, device 100 comprises a fastener or anchor positioned at a distal end of needle 117, wherein actuation of needle 117 pushes the fastener or anchor through respective needle channels 138, out of respective needle channel openings 140, and towards an opposing jaw of grasper 108 (not pictured). Each fastener or anchor can comprise a catch 142 configured to hold a suture thread 130, and can be detached from device 100 after insertion to be left within a target tissue. Contemplated fasteners or anchors include but are not limited to staples, barbs, pins, hooks, spurs, spikes, anchors, and the like. Fasteners or anchors can be biodegradable or non-biodegradable.

The scaffold and suture anchoring devices of the present invention can be made using any suitable method known in the art. The method of making may vary depending on the materials used. For example, components of the device comprising a metal may be milled from a larger block of metal or may be cast from molten metal. Likewise, components of the device substantially comprising a plastic or polymer may be milled from a larger block or injection molded. In some embodiments, the devices may be made using 3D printing or other additive manufacturing techniques commonly used in the art.

Method of Anchoring Scaffold and Suture

Figure 9:
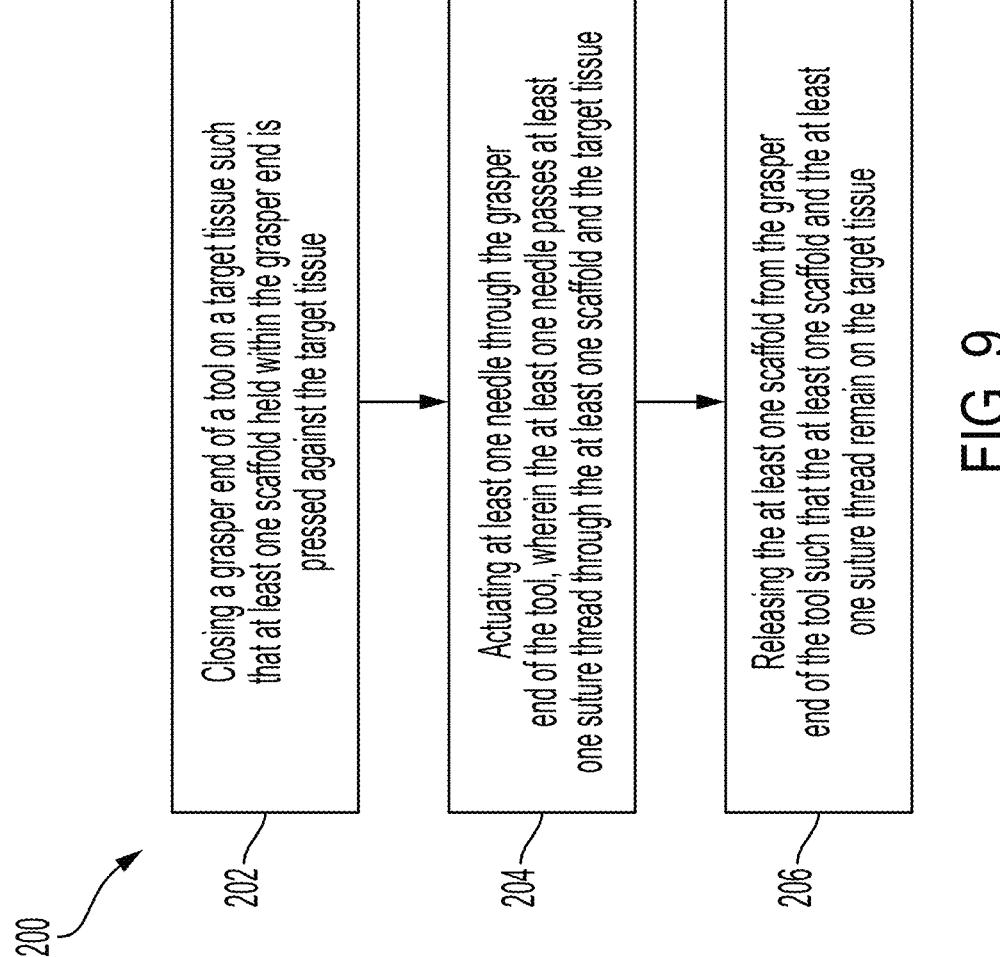
FIG. 9 depicts a flowchart of an exemplary method of anchoring a scaffold and suture to a target tissue.
Figure 10:
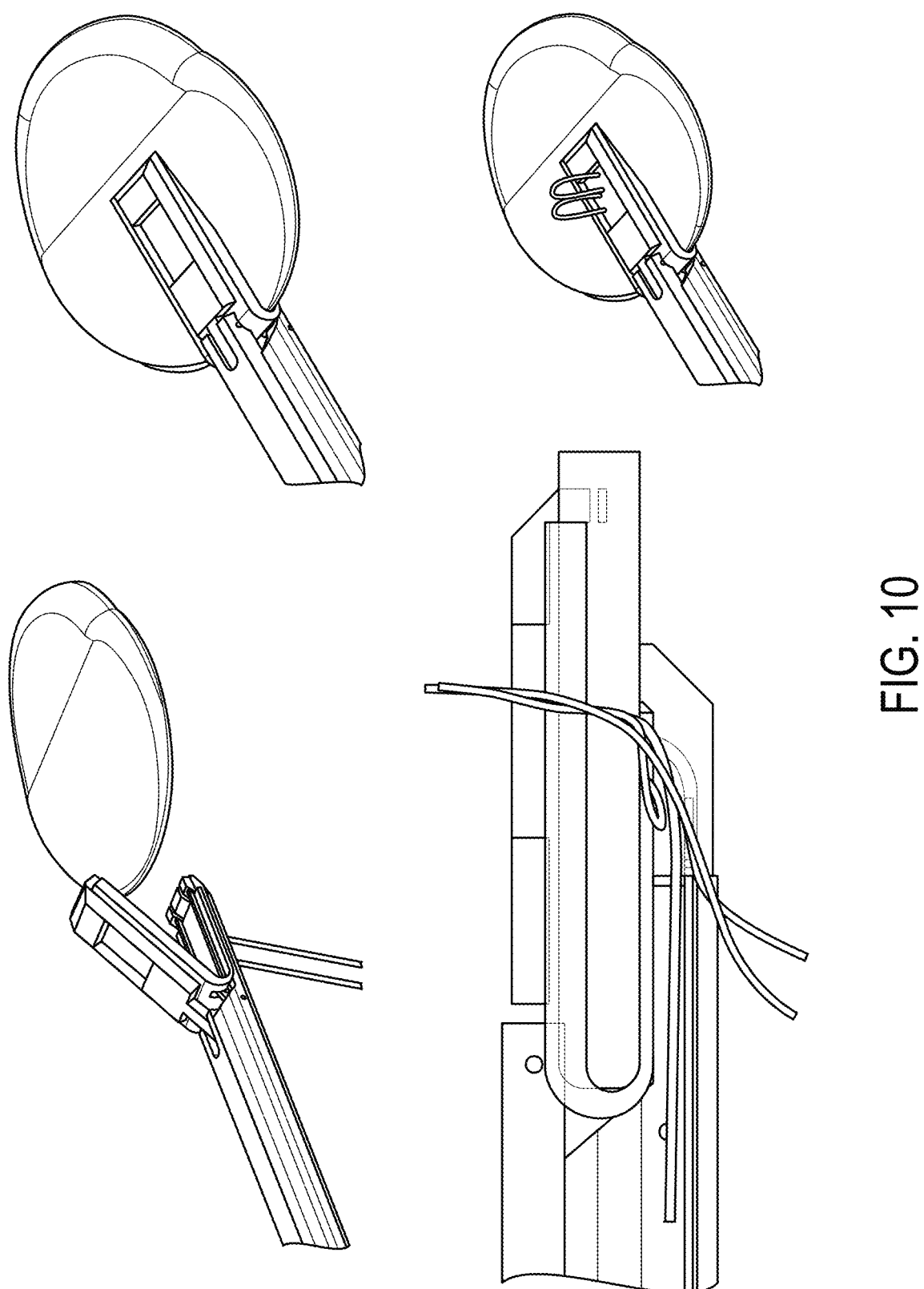
FIG. 10 depicts a schematic of (top left) an exemplary scaffold and suture anchoring device approaching a target tissue, (top right) the device approximating a suture and thread anchoring location, (middle) needles passing a suture thread through soft tissue and scaffold, and (bottom) exposed suture thread remaining in soft tissue and scaffold after needles are retracted.
Figure 11:
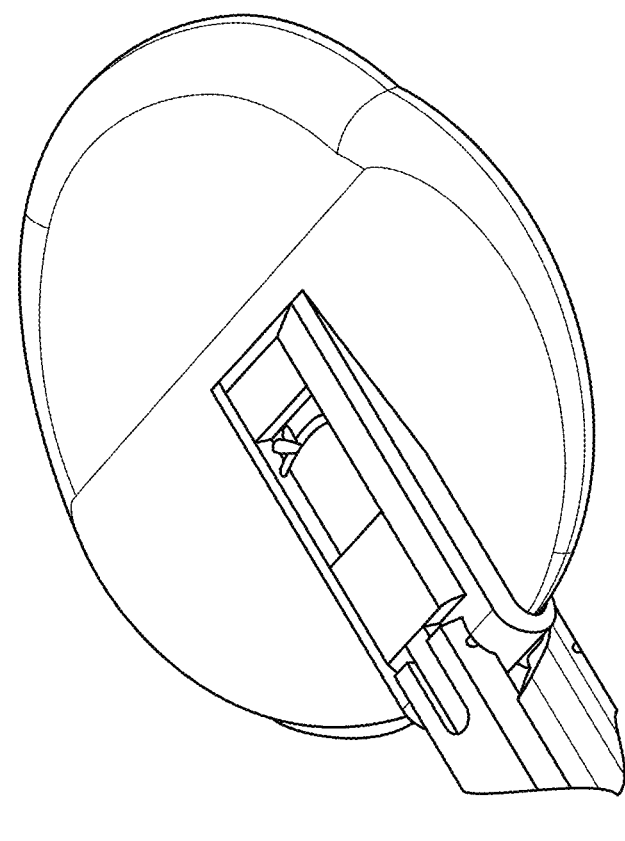
FIG. 11 depicts a schematic of (left) a device retrieving exposed suture thread and (right) suture thread secured to soft tissue and scaffold.
Figure 11:
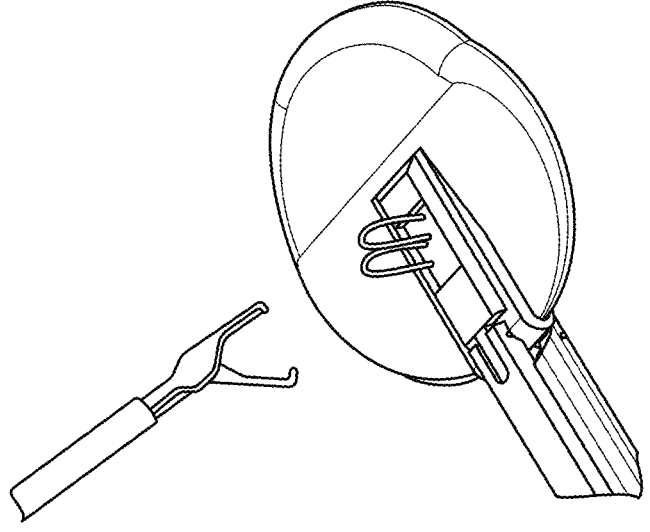
Figure 12:
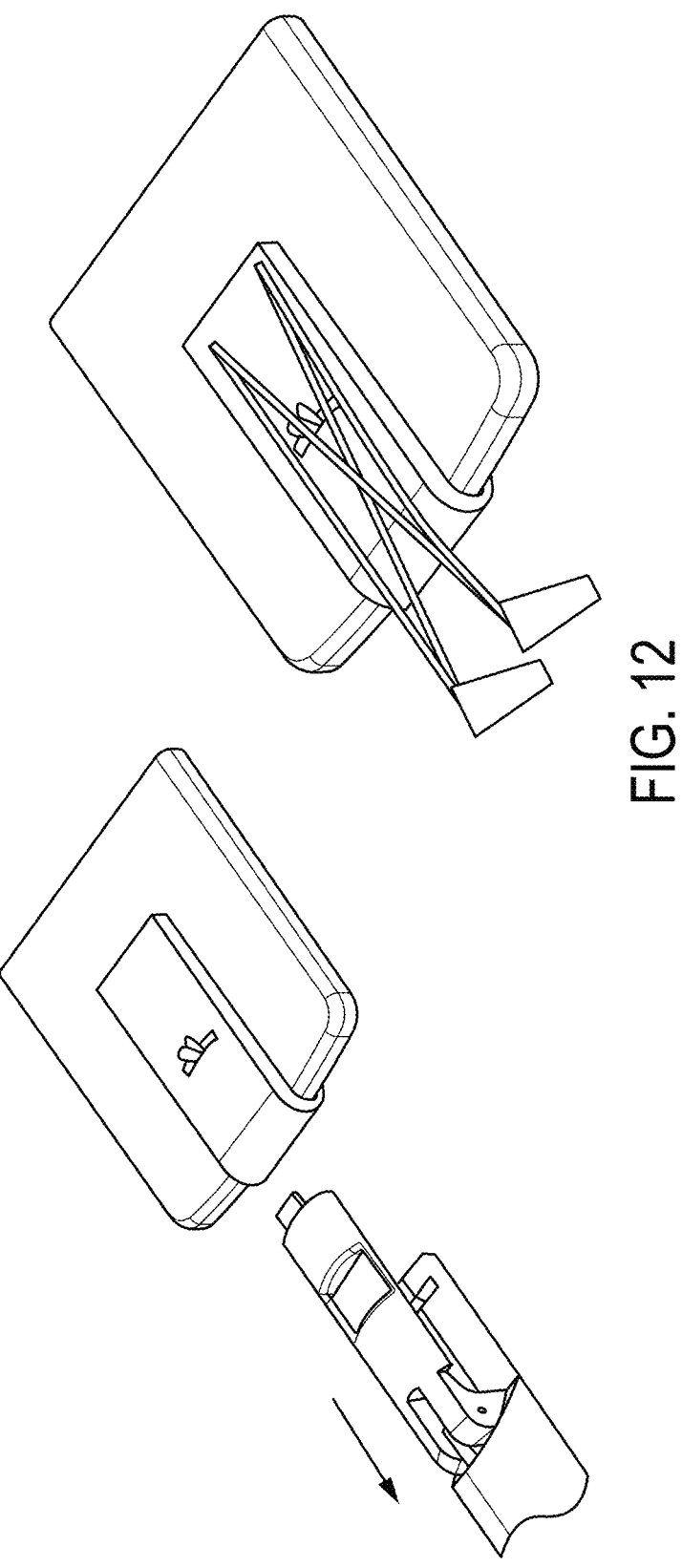
FIG. 12 depicts a schematic of (left) an exemplary scaffold and suture anchoring device withdrawing from a target tissue, leaving behind a scaffold secured to soft tissue by suture thread, and (right) further suturing as desired.

Referring now to FIG. 9, an exemplary method 200 of anchoring scaffold and suture is depicted. Certain steps of method 200 are depicted in FIG. 10 through FIG. 12. Method 200 begins with step 202, wherein a grasper end of a tool is closed on a target tissue such that at least one scaffold held within the grasper end is pressed against the target tissue. In step 204, at least one needle is actuated through the grasper end of the tool, wherein the at least one needle passes at least one suture thread through the at least one scaffold and the target tissue. In step 206, the at least one scaffold is released from the grasper end of the tool such that the at least one scaffold and the at least one suture thread remain on the target tissue.

FIG. 10 illustrates step 202 and step 204. In the top left and top right images, the grasper end of the tool approaches a target tissue and closes on a desired location on the target tissue, such as with a grasper trigger. It should be appreciated that the grasper end can be released from the target tissue and repositioned as many times as needed until accurate placement is achieved. In some embodiments, the method further comprises a step of locking the grasper end of the tool such that the grasper end remains closed on the target tissue until the lock is released. The step of locking the grasper end of the tool can occur between step 202 and step 204.

In the middle image of FIG. 10, a cutaway view of the grasper end of the tool is shown, wherein the at least one needle is actuated through the grasper end to pierce the at least one scaffold and the target tissue, such as with a needle trigger. The at least one suture thread threaded on the at least one needle is passed along with the at least one needle through the at least one scaffold and the target tissue. In some embodiments, the at least one suture thread is pre-threaded on the at least one needle. In some embodiments, the methods further comprise a step of threading at least one suture thread onto the at least one needle. The step of threading at least one suture thread onto the at least one needle can occur prior to step 202. In the bottom image, the at least one needle is retracted, leaving the at least one suture thread passing through the at least one scaffold and the target tissue. It should be noted that after passing through the at least one scaffold and target tissue, a loop of the suture thread is positioned underneath the at least one scaffold and target issue, while a length of each of the two free ends of the suture thread are "inverted" and passed through the at least one scaffold and target tissue. In some embodiments, the methods further comprise a step of retrieving free ends of the at least one suture thread (FIG. 11, left). The at least one retrieved suture thread can be manipulated as desired, such as by securing the at least one scaffold to the target tissue in a knotted or knotless manner (FIG. 11, right).

FIG. 12 (left) illustrates step 206, wherein the at least one scaffold is released from the grasper end of the tool such that the at least one scaffold and the at least one suture thread remain on the target tissue. It should be appreciated that if a step of locking the grasper end of the tool was performed, then it follows that a step of unlocking the grasper end of the tool should precede step 206. In some embodiments, the at least one scaffold is released by sliding retainer tabs of a retainer to withdraw retainer tines from the grasper end of the tool. In some embodiments, the methods further comprise one or more steps of suturing the at least one scaffold to the target and surrounding tissue. For example, FIG. 12 (right) depicts the results of steps of passing sutures from medial row anchors to lateral row anchors.

It should be understood that the orientation of the at least one scaffold relative to the target tissue will depend on how the at least one scaffold was initially loaded on the grasper. For example, in some embodiments a single scaffold wraps between an upper jaw and lower jaw of the grasper end of the tool, in which case the methods anchor the scaffold on a target tissue such that the scaffold wraps around a superior side, a lateral side, and an inferior side of the target tissue. In some embodiments, one or more scaffolds are separately loaded on the upper jaw and lower jaw of the grasper end of the tool, in which case the methods anchor the one or more scaffolds on a target tissue such that the one or more scaffolds rest on a superior side and an inferior side of the target tissue. In some embodiments, one or more scaffolds are loaded only on the upper jaw or only on the lower jaw of the grasper end of the tool, in which case the methods anchor the one or more scaffolds on a target tissue such that the one or more scaffolds rest only on a superior side or an inferior side of the target tissue, respectively.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A scaffold and suture anchoring device, comprising:
an elongated shaft having a proximal end and a distal end;
a handle connected to the proximal end of the shaft, the handle comprising a grasper trigger, a needle trigger, and a retainer tab slot;
a grasper comprising an upper jaw hingedly connected to a lower jaw at the distal end of the shaft, the grasper being mechanically linked to the grasper trigger;
a retainer positioned within a lumen of the shaft, the retainer comprising at least one retainer tab slidable in the retainer tab slot at a proximal end and at least one retainer tine having a distal tip extending through at least one of the upper jaw and the lower jaw of the grasper at a distal end, wherein a portion of the at least one retainer tine proximal of the distal tip is disposed exterior to and between the upper and lower jaw of the grasper; and
at least one needle positioned within a needle channel of the shaft, the needle being mechanically linked to the needle trigger and the needle channel comprising a curved portion;
wherein the needle channel extends to the lower jaw of the grasper and curves towards at least one needle channel opening facing the upper jaw of the grasper; and
wherein a distal tip of the needle is configured to deploy distally away from a distal needle channel opening while a proximal portion of the needle remains in the curved portion of the needle channel.

2. The device of claim 1, wherein the device further comprises at least one suture thread pre-threaded onto the at least one needle.

3. The device of claim 1, wherein the upper jaw comprises a window facing the lower jaw of the grasper, such that the at least one needle channel opening is enclosed by the window when the grasper is in a closed position.

4. The device of claim 1, wherein the grasper trigger comprises a lock configured to lock an instant position of the grasper.

5. The device of claim 4, wherein the mechanical link between the grasper trigger and the grasper comprises a spring force configured to return the grasper to an open position.

6. The device of claim 1, wherein the needle trigger comprises a lock configured to lock an instant position of the needle.

7. The device of claim 6, wherein the mechanical link between the needle trigger and the needle comprises a spring force configured to return the needle to a retracted position.

8. The device of claim 1, wherein the device further comprises at least one scaffold preloaded onto the grasper.

9. The device of claim 8, wherein the at least one scaffold is secured between the upper jaw of the grasper and the at least one retainer tine.

10. The device of claim 8, wherein the at least one scaffold is secured between the lower jaw of the grasper and the at least one retainer tine.

11. The device of claim 8, wherein the at least one scaffold is constructed from a synthetic material selected from the group consisting of: poly(urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly (ethylene glycol), poly(methacrylic acid), polylactic acid (PLA), polyglycolic acids (PGA), poly(lactide-co-gly-colides) (PLGA), nylons, polyamides, polyanhydrides, poly (ethylene-co-vinyl alcohol) (EVOH), polycaprolactone, poly(vinyl acetate) (PVA), polyvinylhydroxide, poly(ethyl-ene oxide) (PEO), polyorthoesters, and combinations thereof.

12. The device of claim 8, wherein the at least one scaffold comprises an anisotropic material.

13. The device of claim 8, wherein the at least one scaffold comprises a biological material selected from the group consisting of: collagen, fibrin, fibrinogen, thrombin, elastin, laminin, fibronectin, hyaluronic acid, chondroitin 4-sulfate, chondroitin 6-sulfate, dermatan sulfate, heparin sulfate, heparin, and keratan sulfate, proteoglycans, polysaccharides (e.g., cellulose and its derivatives), chitin, chitosan, alginic acids, alginates, and combinations thereof.

14. The device of claim 8, wherein the at least one scaffold further comprises a factor selected from the group consisting of: epidermal growth factor (EGF), platelet derived growth factor (PDGF), basic fibroblast growth factor (bFGF), trans-forming growth factor-□ (TGF-□), tissue inhibitors of metalloproteinases (TIMP), antibiotics, bacteriocides, fun-gicides, silver-containing agents, analgesics, nitric oxide releasing compounds, and combinations thereof.

15. The device of claim 8, wherein the at least one scaffold further comprises a population of cells selected from the group consisting of: fibroblasts, osteoblasts, keratinocytes, epithelial cells, endothelial cells, mesenchymal stem cells, embryonic stem cells, and combinations thereof.

16. The device of claim 1, wherein at least a portion of the needle channel proximal of the curved portion is substan-tially parallel to a longitudinal axis of the lower jaw.

17. The device of claim 1, wherein a distal tip of the needle is configured to deploy from the distal needle channel opening in a first direction while a proximal portion of the needle moves in a second direction different than the first direction.

18. The device of claim 1, wherein the needle is config-ured to retract proximally through the curved portion.

19. The device of claim 1, wherein a window in the upper jaw is positioned to align with the distal needle channel opening so that the distal tip of the needle can deploy through the window while a proximal portion of the needle remains in the curved portion of the needle channel.

* * * * *